(12) United States Patent
Ma et al.

(10) Patent No.: US 10,980,979 B2
(45) Date of Patent: Apr. 20, 2021

(54) MAGNETIC SHIELD FOR MEDICAL DEVICES

(71) Applicant: Becton, Dickinson and Company, Franklin Lakes, NJ (US)

(72) Inventors: Yiping Ma, Layton, UT (US); Jeffrey C. O'Bryan, Murray, UT (US); S. Ray Isaacson, Layton, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 387 days.

(21) Appl. No.: 15/154,348

(22) Filed: May 13, 2016

(65) Prior Publication Data

US 2017/0326342 A1 Nov. 16, 2017

(51) Int. Cl.
| | |
|---|---|
| *A61M 25/06* | (2006.01) |
| *A61M 5/158* | (2006.01) |
| *A61M 5/162* | (2006.01) |
| *A61M 25/01* | (2006.01) |
| A61B 90/00 | (2016.01) |
| A61B 17/34 | (2006.01) |
| A61M 5/32 | (2006.01) |
| A61B 17/00 | (2006.01) |

(52) U.S. Cl.
CPC ........ *A61M 25/0612* (2013.01); *A61M 5/158* (2013.01); *A61M 5/1626* (2013.01); *A61M 25/0127* (2013.01); *A61M 25/065* (2013.01); A61B 17/3403 (2013.01); A61B 2017/00876 (2013.01); A61B 2090/3954 (2016.02); A61M 5/3202 (2013.01); A61M 25/0606 (2013.01); A61M 2005/1585 (2013.01); A61M 2205/0272 (2013.01); A61M 2205/0288 (2013.01)

(58) Field of Classification Search
CPC ............ A61M 5/1626; A61M 25/0612; A61M 5/155; A61M 5/3213; A61M 5/3202; A61M 2005/1585; A61M 2205/0288; A61B 17/3403
See application file for complete search history.

(56) References Cited

U.S. PATENT DOCUMENTS

| | | | |
|---|---|---|---|
| 4,161,943 | A | 7/1979 | Nogier |
| 5,000,912 | A | 3/1991 | Bendel et al. |

(Continued)

FOREIGN PATENT DOCUMENTS

| | | |
|---|---|---|
| CN | 201138912 Y | 10/2008 |
| CN | 104853799 A | 8/2015 |

(Continued)

OTHER PUBLICATIONS

PCT International Search Report and Written Opinion in PCT/US2017/031566 dated Aug. 14, 2017, 17 pages.

(Continued)

*Primary Examiner* — Nathan R Price
*Assistant Examiner* — Melissa A Snyder
(74) *Attorney, Agent, or Firm* — Servilla Whitney LLC

(57) ABSTRACT

A medical device such as a needle subassembly is disclosed including a cover over a magnetized portion of a tissue-penetrating medical device having a shielding material associated with the cover that prevents the magnetized portion of the tissue-penetrating medical device from being de-magnetized when the cover is positioned to cover the tissue-penetrating medical device.

21 Claims, 3 Drawing Sheets

(56) References Cited

U.S. PATENT DOCUMENTS

| | | | |
|---|---|---|---|
| 5,359,992 A | | 11/1994 | Hori et al. |
| 5,431,640 A | | 7/1995 | Gabriel |
| 6,432,036 B1 | | 8/2002 | Kim |
| 6,673,999 B1 | * | 1/2004 | Wang ................ B82Y 25/00 174/36 |
| 7,935,080 B2 | | 5/2011 | Howell et al. |
| 9,802,009 B2 | * | 10/2017 | Nessel ................ A61M 5/20 |
| 2002/0042581 A1 | | 4/2002 | Cervi |
| 2004/0249428 A1 | * | 12/2004 | Wang .................. A61F 2/90 607/116 |
| 2005/0004417 A1 | * | 1/2005 | Nelson ................ A61F 2/00 600/12 |
| 2005/0165301 A1 | | 7/2005 | Smith et al. |
| 2007/0049846 A1 | | 3/2007 | Bown et al. |
| 2007/0255211 A1 | * | 11/2007 | Young ............... A61B 50/362 604/110 |
| 2009/0012517 A1 | | 1/2009 | De La Rama et al. |
| 2009/0032499 A1 | | 2/2009 | Tenne et al. |
| 2010/0036238 A1 | | 2/2010 | Neidert et al. |
| 2010/0217275 A1 | | 8/2010 | Carmeli et al. |
| 2010/0228119 A1 | * | 9/2010 | Brennan ............ A61B 5/0066 600/424 |
| 2011/0196397 A1 | | 8/2011 | Frantz et al. |
| 2012/0041297 A1 | | 2/2012 | McGary |
| 2013/0131547 A1 | | 5/2013 | Hardert et al. |
| 2014/0031674 A1 | | 1/2014 | Newman et al. |
| 2014/0046261 A1 | * | 2/2014 | Newman .......... A61M 25/0127 604/158 |
| 2014/0135595 A1 | | 5/2014 | Powell et al. |
| 2014/0253270 A1 | * | 9/2014 | Nicholls ............. A61B 5/062 335/284 |
| 2014/0257080 A1 | | 9/2014 | Dunbar et al. |
| 2014/0276539 A1 | * | 9/2014 | Allison ............... A61B 18/02 604/500 |
| 2015/0080710 A1 | | 3/2015 | Henkel et al. |
| 2015/0306319 A1 | * | 10/2015 | Nessel ................ A61M 5/20 604/111 |
| 2015/0320977 A1 | | 11/2015 | Vitullo et al. |
| 2015/0359991 A1 | | 12/2015 | Dunbar et al. |
| 2017/0232204 A1 | | 8/2017 | Knapp et al. |

FOREIGN PATENT DOCUMENTS

| | | |
|---|---|---|
| EP | 2730306 A2 | 5/2014 |
| JP | S5816599 A | 1/1983 |
| JP | S61160998 A | 7/1986 |
| JP | 2015535714 A | 12/2015 |
| WO | 02/083208 A2 | 10/2002 |
| WO | 2009061860 A1 | 5/2009 |
| WO | 2014052894 A1 | 4/2014 |

OTHER PUBLICATIONS

PCT International Search Report in PCT/US2017/031572 dated Aug. 24, 2017, 14 pages.

Nave, R. , "Ferromagnetism [online], Georgia State University, HyperPhysics, Jul. 1, 2006 [retrieved on Oct. 12, 2018].", Retrieved from the internet: <URL: https://web.archive.org/web/20060701023036/http://hyperphysics.phyastr.gsu.edu/hbase/Solids/ferro.html>, 1 page.

Final Office Action in U.S. Appl. No. 15/154,353 dated Jul. 12, 2019, 12 pages.

Non-Final Office Action in U.S. Appl. No. 15/154,353 dated Mar. 19, 2019, 12 pages.

Non-Final Office Action in U.S. Appl. No. 15/170,531 dated Sep. 6, 2019, 41 pages.

Non-Final Office Action in U.S. Appl. No. 15/604,244 dated Jun. 27, 2019, 50 pages.

Honnegowda, Lakshmisha , et al., "Security Enhancement for Magnetic Data Transaction in Electronic Payment and Healthcare Systems [online]", IACSIT International Journal of Engineering and Technology, Apr. 2013 [retrieved on Sep. 5, 2019], vol. 5, No. 2.

Final Office Action in U.S. Appl. No. 15/170,497 dated Jun. 23, 2020, 40 pages.

Final Office Action in U.S. Appl. No. 15/154,353 dated Jun. 24, 2020, 12 pages.

* cited by examiner

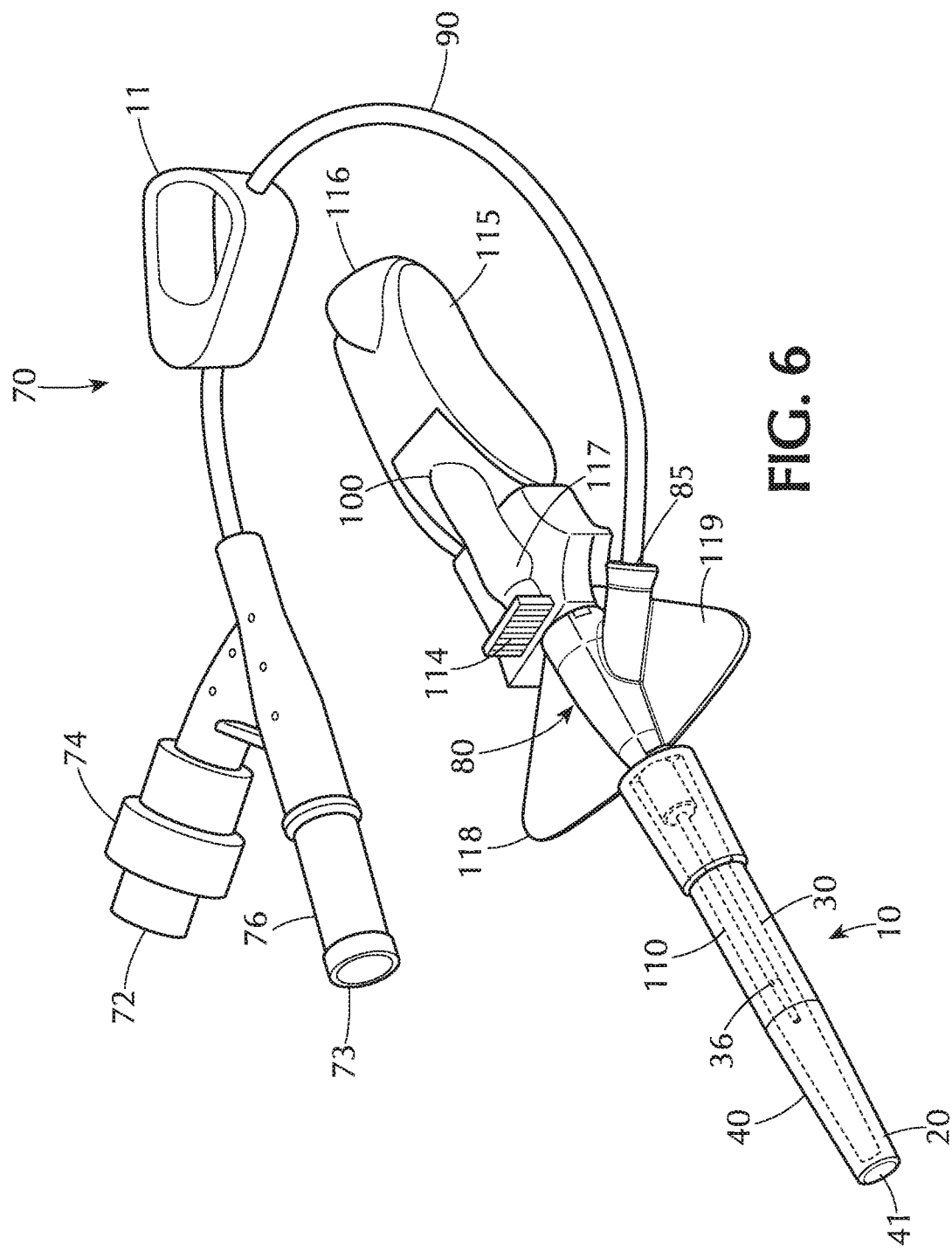

MAGNETIC SHIELD FOR MEDICAL DEVICES

FIELD

Aspects of the present disclosure relate to a magnetic shield for medical devices having a cover sized to provide a protective closure over a magnetized portion of a tissue-penetrating medical device with a shielding material associated with the cover that prevents the magnetized portion of the tissue-penetrating medical device from being de-magnetized when the cover is positioned to cover the tissue-penetrating medical device.

BACKGROUND

Traditionally, penetration of an invasive medical device such as a needle and catheter tubing through skin tissue to reach the vein during catheter insertion is invisible to clinicians. For this reason, clinicians must rely on their first-hand experience with needle insertion in combination with tactile sense to successfully identify the location of the vein. This may be a difficult task when attempting to access a small vein in a deep location under the skin, increasing risk of excess pain and/or injury to the patient. There are similar problems with insertion of other invasive medical devices such as guidewires, catheter introducers and stylets with respect to the inability to precisely visualize the location of the invasive medical device.

Emerging procedural guidance systems utilize a combination of ultrasound and magnetic technologies to provide visualization of subdermal anatomy and device position in the in-plane and out-of-plane orientations. This combination of ultrasound and magnetic methods also allows for the projection or anticipation of the insertion device position relative to the patient's anatomy, and thereby improves the likelihood of successfully accessing the vascular and completing the invasive procedure.

Ultra-sound and magnetic procedural guidance system technology relies on the invasive device having a sufficient magnetic field source that can be achieved by embedding a magnet in a known position on the device, or by using an externally applied magnetic field to magnetize a portion of the invasive device prior to insertion. The ultra-sound and magnetic procedural guidance system technology requires that the invasive device have a sufficient magnetic field source that is maintained throughout the procedure. It is important that the magnetized invasive device does not become de-magnetized before being used in a medical procedure.

Thus, there is a need for a protective closure over a magnetized portion of a tissue-penetrating medical device with a shielding material associated with the cover that prevents the magnetized portion of the tissue-penetrating medical device from being de-magnetized when the cover is placed over the tissue-penetrating medical device.

SUMMARY

A first aspect of the disclosure pertains to a needle subassembly. In a first embodiment, the needle subassembly comprises a needle including a shaft having a magnetized portion, and a cover sized to provide a protective closure over a magnetized portion of the shaft and a shielding material associated with the cover that prevents the magnetized portion of the tissue-penetrating medical device from being de-magnetized when the cover is positioned to cover the shaft.

In one embodiment, the shielding material may be a highly conductive material such as copper.

In another embodiment, the shielding material has a high magnetic permeability. The high magnetic permeability shielding material may be an alloy of nickel and iron metals. In a specific embodiment, the shielding material includes a ferromagnetic metal coating.

In yet another embodiment, the shielding material includes both a highly conductive material and a ferromagnetic metal coating. The highly conductive material may be copper and the high magnetic permeability shielding material may be an alloy of nickel and iron metals.

In one or more embodiments, the cover of the needle subassembly is in the form of a needle cover, catheter packaging or shipping container.

In one or more embodiments, the shielding material may be spray-coated onto an interior surface or exterior surface of the cover.

In another embodiment, the shielding material may be spray-coated onto an interior surface and exterior surface of the cover.

In yet another embodiment, the shielding material may be insert-molded into the cover.

The cover may be molded from a plastic having conductive additives or from a plastic having magnetic additives. The cover may also be made entirely of a magnetic shielding material.

A second aspect of the disclosure pertains to a medical device or vascular access device comprising a tissue-penetrating element and a cover sized to provide a protective closure over a magnetized portion of the tissue-penetrating medical device, wherein the cover comprises a shielding material that prevents the magnetized portion of the tissue-penetrating medical device from being de-magnetized when the cover is positioned to cover the tissue-penetrating medical device.

In one or more embodiments of the medical device, the shielding material may be spray-coated onto an interior or exterior surface of the cover.

In another embodiment of the medical device, the shielding material is insert-molded into the needle cover.

The tissue-penetrating medical device may be a needle, cannula, stylet or catheter. The tissue-penetrating medical device may be made of a magnetizable metallic material. In one embodiment, the magnetizable metallic material is stainless steel. In a specific embodiment, the tissue-penetrating element comprises an introducer needle having a length and a tip portion wherein the cover is sized to cover the tip and the length of the introducer needle.

BRIEF DESCRIPTION OF THE DRAWINGS

FIG. 6 is a perspective view of one or more embodiments of a vascular access device including an embodiment of a magnetic shield of the present disclosure.

DETAILED DESCRIPTION

Figure 1:
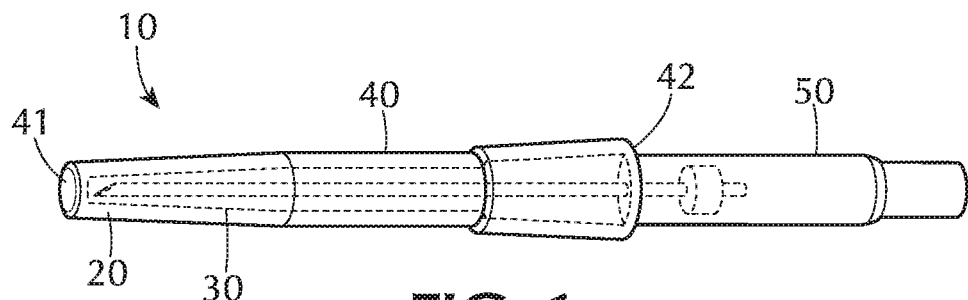
FIG. 1 illustrates a perspective view of an embodiment of a magnetic shield of the present disclosure.

Before describing several exemplary embodiments of the disclosure, it is to be understood that the description provided is not limited to the details of construction or process steps set forth in the following description. The magnetic shield and medical devices described herein are capable of other embodiments and of being practiced or being carried out in various ways.

In this disclosure, a convention is followed wherein the distal end of the device is the end closest to a patient and the proximal end of the device is the end away from the patient and closest to a practitioner.

Magnetized regions in a catheter, such as a needle, have been used to guide catheter insertion into a patient in conjunction with ultrasound. Catheter placement using magnetized catheter components, such as a needle tip, requires at least one section of the needle to be magnetized at some desired length. The magnetization step can be accomplished during the catheter manufacturing process or at the time of catheter placement as currently available. For magnetizing the needle at the time of placement, the current technology requires the clinician to manually magnetize the needle in a disposable magnetizer prior to inserting the catheter into a patient. Current procedures for magnetic and ultrasound procedural guidance systems rely on the user to place an un-protected needle within the disposable needle magnetizer to a depth defined by the bottom of the magnetizer. Given the potential inconsistency of the user to complete this step, there exists significant risk of damaging the needle tip, along with an increased potential for microbial contamination during a user-based magnetizing procedure. In addition, it is costly to discard the magnetizer after each catheter placement. Therefore, it would be advantageous to have a system that allows the magnetic component, such as the needle, to be magnetized during catheter manufacturing process and which allows the needle to remain magnetized until ready for use. Magnetizing the magnetic component during the catheter manufacturing process would yield consistency in both the length of the magnetized section of the magnetic component and the resultant strength of the magnetic field. In addition, it would not require the user to perform the additional step of magnetization in the field, thus causing no change in catheter placement steps.

Therefore, magnetization during manufacturing is preferred due to its control in consistency and unlikelihood of damage to the catheter tip due to handling. However, when the catheter with a magnetized region leaves the manufacturing plant, it could be subject to external magnetic and/or electromagnetic fields that may weaken the magnetic force of the magnetized region. Such external magnetic and/or electromagnetic fields could be strong enough to overcome the coercivity of the magnetized region and de-magnetize the magnetized region. Therefore it is desirable to shield the magnetized region from the external fields. Once shielded, the external field will not reach the magnetized region to de-magnetize the magnetized region.

As shown in FIG. 1, one aspect of the disclosure pertains to a magnetic shield 10 for a medical device 50 which comprises a cover 20 sized to provide a protective closure over a magnetized portion of a tissue-penetrating medical device 50, a shielding material 30 associated with the cover 20 that prevents the magnetized portion of the tissue-penetrating medical device from being de-magnetized when the cover 20 is placed over the tissue-penetrating medical device 50. In the embodiment shown, the tissue penetrating medical device 50 is in the form of a needle subassembly. In one or more embodiments, the magnetized portion of the tissue-penetrating medical device may comprise a partial length of the tissue-penetrating medical device. In one or more embodiments, the magnetized portion of the tissue-penetrating medical device may comprise a distal tip of the tissue-penetrating medical device. In one or more embodiments, the magnetized portion of the tissue-penetrating medical device may comprise an entire length of the tissue-penetrating medical device.

The cover 20 may include a plastic sleeve member having a hollow tubular body 40 having a closed end 41 and an opposing open end 42 to form a protective closure over the tissue-penetrating medical device 50. The sleeve member may be substantially coextensive in length with the length of the tissue-penetrating medical device 50.

Figure 2:
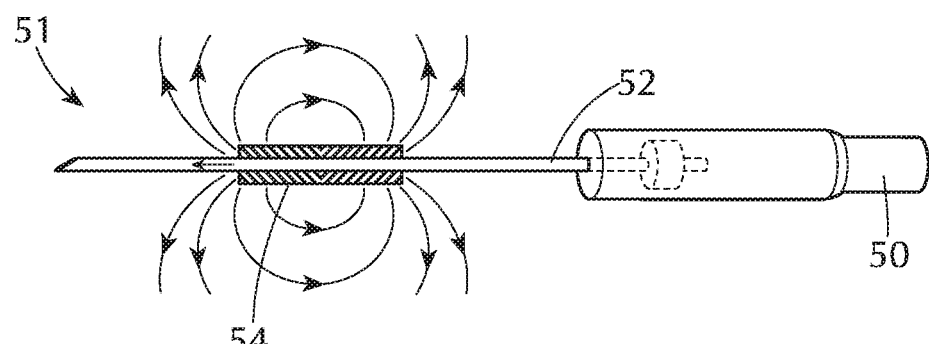
FIG. 2 shows an embodiment of a tissue-penetrating medical device prior to insertion into a magnetic shield of the present disclosure.
Figure 3:
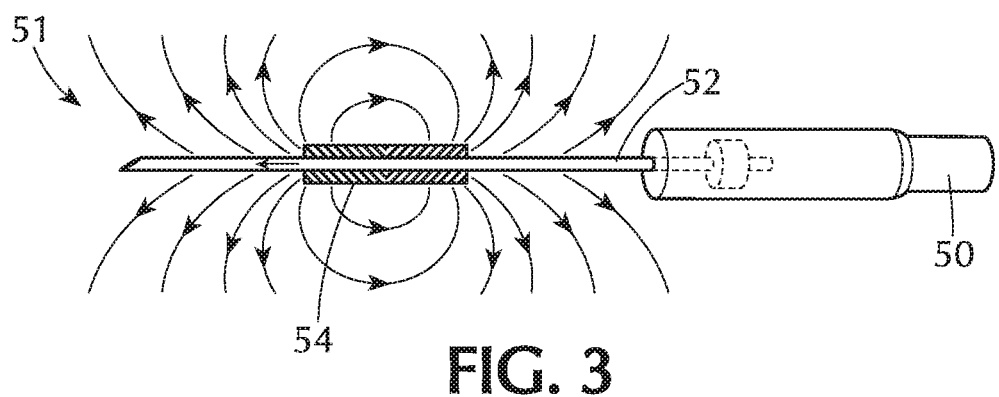
FIG. 3 shows an embodiment of a tissue-penetrating medical device prior to insertion into a magnetic shield wherein the magnetic field extends the entire length of the tissue-penetrating device of the present disclosure.

FIG. 2 shows a tissue-penetrating medical device 50 in the form of a needle subassembly including a needle 51 having a shaft 52 and a magnetized region 54. FIG. 3 shows an embodiment of a tissue-penetrating medical device prior to insertion into a magnetic shield wherein the magnetized region extends the entire length of the tissue-penetrating device from the distal tip to the proximal end of the tissue-penetrating medical device of the present disclosure.

Figure 4:
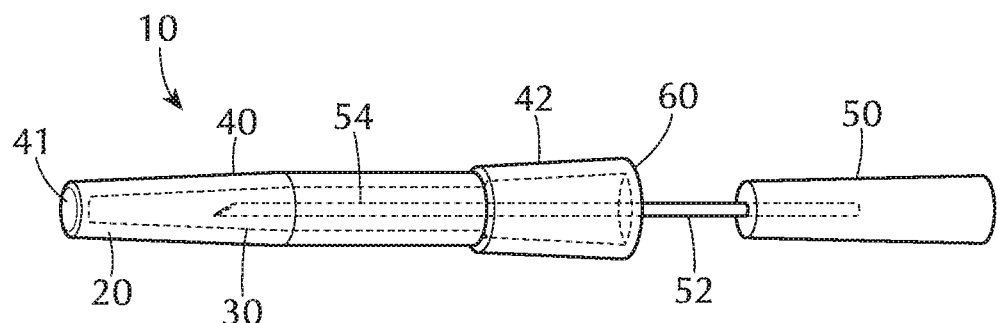
FIG. 4 illustrates a cross-section profile of an embodiment of a tissue-penetrating medical device partially inserted into a magnetic shield of the present disclosure.

As shown in FIG. 4, the open end 42 of the hollow tubular body 40 provides a receiving space 60 for receiving at least part of the tissue-penetrating medical device 50. In the embodiment shown, the part received is the shaft 54 of a needle subassembly. The device-receiving space 60 permits movement of the shaft 54 of the tissue-penetrating medical device 50 into and out of the device-receiving space 60. As shown in FIGS. 3 and 4, the magnetic shield 10 isolates the magnetized region of the tissue-penetrating medical device 50 from any external magnetic and electromagnetic fields thus keep the integrity of the magnetization of the magnetized region. Thus, the magnetic shield 10 is capable of shielding a magnetized region in a catheter from being de-magnetized after leaving a manufacturing facility and prior to catheter placement in patient.

Figure 5:
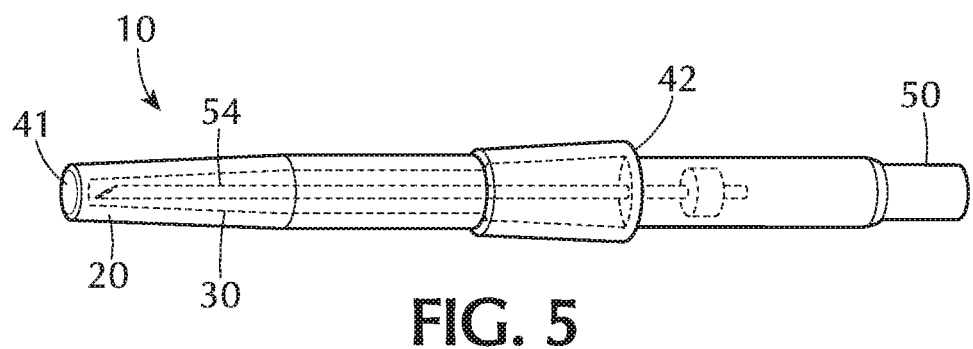
FIG. 5 illustrates a cross-section profile of an embodiment of a tissue-penetrating medical device fully inserted into a magnetic shield of the present disclosure.

In one or more embodiments, as shown in FIG. 5, the magnetic shield 10 contains the magnetic field generated by the magnetized region within the confines of the cover 20 to prevent the magnetized tissue-penetrating medical device 50 from causing magnetic interferences to sensitive equipment and devices in a hospital setting. The magnetic shield 10 would consist of some shielding material 30 which would enclose the magnetized region.

In one or more embodiments, the shielding material 30 may be a highly conductive material, such as copper or copper spray. A highly conductive shielding material will work in the presence of high frequency electromagnetic field. The varying magnetic field will generate eddy current within the conductor which would then cancel the magnetic field, preventing the magnetic field from reaching the magnetized region.

In one or more embodiments, the shielding material 30 may have a high magnetic permeability. In one or more embodiments, the high magnetic permeability material may be iron, nickel, cobalt or an alloy or compounds containing one or more of these elements. In one or more embodiments, the high magnetic permeability material is comprised of an alloy of nickel and iron metals. The high magnetic permeability material may be Permalloy (a nickel-iron magnetic alloy, typically having about 80% nick and about 20% nickel) or ferromagnetic metal coating. In one or more embodiments, the shielding material may be composed of a nickel—iron alloy having approximately 77% nickel, 16% iron, 5% copper and 2% chromium or molybdenum. In yet another embodiment, the shielding material maybe composed of approximately 80% nickel, 5% molybdenum, small amounts of various other elements such as silicon, and the remaining 12 to 15% iron. A high magnetic permeability shielding material will work well in the presence of static external magnetic fields. When an external static magnetic field is present near the magnetized region, the magnetic field line is drawn within the shield due to its high permeability, thus preventing the magnetic field from reaching the magnetized region.

If both a high frequency electromagnetic field and static external magnetic fields are expected to be present, the magnetic shield can consist of both highly conductive shielding material and high magnetic permeability material to block the external magnetic field from reaching the magnetized region. In a specific embodiment, the shielding material 30 includes a highly conductive material and a ferromagnetic metal coating. The highly conductive material may be copper.

Depending on the magnetized region of the catheter, the magnetic shield may be in the form of or incorporated into a needle cover, individual catheter wrapper, catheter dispenser, or a catheter shipper.

According to one embodiment, the shielding material 30 may be spray-coated onto an interior surface of the cover or an exterior surface of the cover. In another embodiment, the shielding material 30 may be spray-coated onto an interior surface and exterior surface of the cover. In one or more embodiments, the shielding material may be spray-coated onto an interior surface of the cover or an exterior surface of the cover to a thickness of $\frac{1}{1000}^{th}$ of an inch to 1 inch. The thickness of the shielding material may depend on the desired purpose or application of the medical device.

In another embodiment, the shielding material 30 may be insert-molded into the cover.

According to one or more embodiments, the cover 20 may be molded from a plastic having conductive additives or magnetic additives. In one embodiment, the cover 20 may be sterile and/or disposable.

According to one or more embodiments, the cover 20 may be made entirely of a magnetic shielding material. The shielding material 30 may be a highly conductive material, such as copper.

When the magnetic shield is incorporated into individual medical device packaging, the entire packaging can be coated with the shielding material 30. Alternatively, only the sections of the packaging enclosing the magnetized regions may contains the magnetic shielding material. Such approach would facilitate ease of sterilization through the packaging. FIG. 2 shows an embodiment with a magnetized needle ready for insertion after cover 20 has been removed. This allows the device to be used with the procedural guidance systems that utilize magnetic sensors as a means of measuring and predicting needle tip location relative to the target anatomy.

Another aspect relates to a medical device which comprises a tissue-penetrating device and a cover 20 sized to provide a protective closure over a magnetized portion of the tissue-penetrating medical device. The cover 20 includes a shielding material 30 that prevents the magnetized portion of the tissue-penetrating medical device from being de-magnetized when the cover 20 is placed over the tissue-penetrating medical device 50.

In one or more embodiments, the tissue-penetrating medical device may be a needle, cannula, stylet or catheter. The tissue-penetrating medical device 50 is made of a magnetizable metallic material. In a specific embodiment, the magnetizable metallic material is stainless steel.

The cover 20 prevents the magnetized portion of the tissue-penetrating medical device from being de-magnetized when the cover is placed over the tissue-penetrating medical device. In one embodiment, the tissue-penetrating medical device is a magnetized needle which may be used with a procedural guidance system to locate and project the position of the needle during an invasive medical procedure.

In one embodiment, the tissue-penetrating device may comprise an introducer needle having a length and a tip portion. The cover 20 is sized to cover the tip and the length of the introducer needle.

The magnetic shield 10 described with respect to FIGS. 1-4 can be used as part of a vascular access device described with respect to FIG. 5.

As shown in FIG. 6, another aspect of the disclosure pertains to a vascular access device 70 comprising a catheter 110 having a proximal end and a distal end; a catheter adapter having a distal end, a proximal end, an overall length extending from the distal end to the proximal end, an internal cavity, an upper portion, a lower portion and a tip region having a distal opening having a circumference through which the catheter extends, the catheter adapter being connected to the proximal end of the catheter; an introducer needle 36 extending through the catheter; a needle hub connected to the proximal end of the introducer needle, and a magnetic shield 10 which comprises a cover 20 including a plastic sleeve member having a hollow tubular body 40 having a closed end 41 and an opposing open end to form a protective closure over a magnetized portion of the introducer needle, a shielding material 30 associated with the cover 20 that prevents the magnetized portion of the tissue-penetrating medical device from being de-magnetized when the cover 20 is placed over the tissue-penetrating medical device.

In one or more embodiments, the shielding material 30 is a highly conductive material. In one embodiment, the highly conductive material comprises copper.

In one or more embodiments, the shielding material 30 has a high magnetic permeability. In one embodiment, the shielding material comprises alloy of nickel and iron metals.

In one embodiment, the shielding material 30 includes a ferromagnetic metal coating. In yet another embodiment, the shielding material includes a highly conductive material and a ferromagnetic metal coating.

The shielding material 30 may be spray-coated onto a surface of the cover, either an interior surface or exterior surface. In another embodiment, the shielding material may be spray-coated onto both an interior surface and exterior surface.

The shielding material 30 may be insert-molded into the cover 20. Insert molding combines metal and thermoplastic materials, or multiple combinations of materials and components into a single unit. Insert molding processes typically involve an injection molding process in which solid pellets of raw material are melted and extruded into a mold—the plastic is then solidified—and then the press opens and the molded parts are ejected. The component to be insert-molded is placed in the mold, either by hand, or by automation before the material is injected into the mold. Then, as the material flows into features in the insert, the insert is anchored much more securely than if it were assembled to a previously molded component.

As shown in FIG. 6, the magnetic shield 10 may be part of a vascular access device 70, with additional components in fluid communication with a catheter adapter 80. As shown in FIG. 6, the lateral access port 85 may be connected to a section of extension tube 90 for establishing fluid communication between an intravenous fluid source and the internal cavity of the catheter adapter or lumen of the catheter. In one or more embodiments, the extension tube 90 extends in line with or laterally with the body of the catheter adapter. In one or more embodiments, the extension tube 90 is built-in to reduce contamination and mechanical phlebitis by eliminating manipulation at the insertion site. In one or more embodiments, the extension tube 90 is compatible with high pressure injection. In one or more embodiments, the extension tube 90 provides continuous confirmation of vessel access during advancement of the catheter into the patient's vein.

In one or more embodiments, needle hub assembly 100 is assembled with the catheter adapter by inserting the needle into the lumen of the catheter 110. The needle hub assembly is shown as including finger grips 115 positioned at the sides of the needle hub assembly 100 to facilitate various insertion techniques. In one or more embodiments, bumps may be present on the finger grip to indicate where to the user may grip the device for needle removal. In one or more embodiments, a thumb pad 116, having a gently convex surface, is provided at the proximal end of the needle hub assembly 100. A flange 117, having a gently convex surface, is provided at the proximal end of the hub assembly to provide a finger pad.

First wing members 118, second wing member 119, thumb pad 116 and flange 117 may be utilized by the user during insertion, permitting the user to elect which insertion technique to employ.

In one or more embodiments, the flange 117 may also include a needle shield. The needle shield may be a design adapted to secure the tip of the needle within the shield after use. In one or more embodiments, the needle shield may be activated passively to ensure compliance with compromising user technique. The needle tip is completely covered by the needle shield in a fixed position. In one or more embodiments, a ferrule, crimp or other structure may be included near the tip for engagement with a needle shield in certain applications.

A push tab 114 may be provided to facilitate catheter advancement during insertion. The push tab also allows for one-handed or two-handed advancement. In one or more embodiments, the push tab is removed with the needle shield. A clamp may also be included on the extension tubing to prevent blood flow when replacing the access port.

The proximal end of the introducer needle may be crimped to provide a fluid-tight seal around the proximal end of the introducer needle. The introducer needle may be glued or mechanical interlocks may be formed to secure the introducer needle to the hub.

In one or more embodiments, the vascular access device 70 further includes a first luer access 72 and a second luer access 73 in fluid communication with the extension tube 90, a blood control split septum 74 associated with the first luer access 72, and an air vent 76 associated with the second luer access 73. Split septum 74 allows for a reduction in catheter-related bloodstream infection CRBSI while providing unrestricted flow and a straight fluid path and functions as a blood control septum. In one or more embodiments, the split septum 74 may be located in an internal cavity of the catheter adapter or on the distal end of the catheter adapter. In yet another embodiment, the split septum 74 may be located on a distal end of the extension tube 60. The air vent 76 allows air to escape from the system during insertion, providing continuous confirmation of vascular access while preventing leakage of blood from the system during insertion. In one or more embodiments, the air vent 76 may be at the distal end of extension tube 90.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A needle subassembly comprising:
   a needle including a shaft having a magnetized portion; and
   a magnetic shield comprising a removable cover sized to provide a protective closure over the magnetized portion of the shaft and a shielding material that prevents the magnetized portion of the shaft from being demagnetized when the cover is positioned to cover the shaft;
   wherein the removable cover is removed prior to insertion;
   wherein the magnetic shield includes a highly conductive material and a ferromagnetic metal coating.

2. The needle subassembly of claim 1, wherein the shielding material has a high magnetic permeability.

3. The needle subassembly of claim 1, wherein the highly conductive material comprises copper.

4. The needle subassembly of claim 1, wherein the cover is selected from a needle cover, catheter packaging or a shipping container.

5. The needle subassembly of claim 1, wherein the shielding material is spray-coated onto an interior surface of the cover.

6. The needle subassembly of claim 1, wherein the shielding material is spray-coated onto an exterior surface of the cover.

7. The needle subassembly of claim 1, wherein the shielding material is spray-coated onto an interior surface and exterior surface of the cover.

8. The needle subassembly of claim 1, wherein the shielding material is insert-molded into the cover.

9. The needle subassembly of claim 1, wherein the cover is molded from a plastic having conductive additives.

10. The needle subassembly of claim 1, wherein the cover is molded from a plastic having magnetic additives.

11. The needle subassembly of claim 1, wherein the cover is made of a magnetic shielding material.

12. The needle subassembly of claim 11, wherein the shielding material is a highly conductive material.

13. The needle subassembly of claim 11, wherein the shielding material has a high magnetic permeability.

14. A medical device comprising:
a tissue-penetrating device having a magnetized portion; and
a magnetic shield comprising a removable cover sized to provide a protective closure over the magnetized portion of the tissue-penetrating medical device, wherein the cover comprises a shielding material that prevents the magnetized portion of the tissue-penetrating medical device from being de-magnetized when the cover is positioned to cover the tissue-penetrating medical device;
wherein the removable cover is removed prior to insertion;
wherein the magnetic shield includes a highly conductive material and a ferromagnetic metal coating.

15. The medical device of claim 14, wherein the shielding material has a high magnetic permeability.

16. The medical device of claim 14, wherein the shielding material is spray-coated onto a surface of the cover.

17. The medical device of claim 16, wherein the surface of the cover is an interior surface.

18. The medical device of claim 16, wherein the surface of the cover is an exterior surface.

19. The medical device of claim 14, wherein the shielding material is insert-molded into the cover.

20. The medical device of claim 14, wherein the tissue-penetrating device comprises an introducer needle having a length and a tip, and the cover is sized to cover the tip and the length of the introducer needle.

21. The needle subassembly of claim 1, wherein the shielding material is composed of 77% nickel, 16% iron, 5% copper and 2% chromium or molybdenum.

* * * * *